US00PP21625P2

(12) United States Plant Patent
Hooijman

(10) Patent No.: US PP21,625 P2
(45) Date of Patent: Jan. 11, 2011

(54) *ASTER* PLANT NAMED 'ESM A002'
(50) Latin Name: *Aster hybrida*
Varietal Denomination: ESM A002

(75) Inventor: Aloysius A. J. Hooijman, Aalsmeer (NL)
(73) Assignee: Esmeralda Breeding B.V., Aalsmeer (NL)

( * ) Notice: Subject to any disclaimer, the term of this patent is extended or adjusted under 35 U.S.C. 154(b) by 0 days.
(21) Appl. No.: 12/587,430
(22) Filed: Oct. 7, 2009
(51) Int. Cl.
*A01H 5/00* (2006.01)
(52) U.S. Cl. ..... Plt./355
(58) Field of Classification Search ..... Plt./355
See application file for complete search history.

*Primary Examiner*—June Hwu
(74) *Attorney, Agent, or Firm*—C. A. Whealy

(57) ABSTRACT

A new and distinct cultivar of *Aster* plant named 'ESM A002', characterized by its strong and erect flowering stems; symmetrical and uniform branching habit with long lateral stems; uniform and freely flowering habit; single-type inflorescences with white-colored ray florets; and good postproduction longevity.

1 Drawing Sheet

Botanical designation: *Aster hybrida.*
Cultivar denomination: 'ESM A002'.

BACKGROUND OF THE INVENTION

The present invention relates to a new and distinct cultivar of *Aster* plant, botanically known as *Aster hybrida*, commercially grown as a cut flower and hereinafter referred to by the name 'ESM A002'.

The new *Aster* plant is a product of a planned breeding program conducted by the Inventor in El Quinche, Pichincha, Ecuador. The objective of the breeding program is to create new cut flower *Aster* plants with dense and compact inflorescences, good productivity and excellent postproduction longevity.

The new *Aster* plant originated from an open-pollination in February, 2004 in El Quinche, Pichincha, Ecuador of a proprietary selection of *Aster hybrida* identified as Line 51, not patented, as the female, or seed, parent with an unknown selection of *Aster hybrida* as the male, or pollen, parent. The new *Aster* plant was discovered and selected by the Inventor as a single flowering plant from within the progeny of the stated open-pollination in a controlled greenhouse environment in El Quinche, Pichincha, Ecuador in February, 2005.

Asexual reproduction of the new *Aster* plant by terminal cuttings in a controlled greenhouse environment in El Quinche, Pichincha, Ecuador since April, 2005, has shown that the unique features of this new *Aster* plant are stable and reproduced true to type in successive generations.

SUMMARY OF THE INVENTION

Plants of the new *Aster* have not been observed under all possible environmental conditions. The phenotype may vary somewhat with variations in environment such as temperature and light intensity, without, however, any variance in genotype.

The following traits have been repeatedly observed and are determined to be the unique characteristics of 'ESM A002'. These characteristics in combination distinguish 'ESM A002' as a new and distinct cultivar of *Aster:*

1. Strong and erect flowering stems.
2. Symmetrical and uniform branching habit with long lateral stems.
3. Uniform and freely flowering habit.
4. Single-type inflorescences with white-colored ray florets.
5. Good postproduction longevity.

Plants of the new *Aster* differ from plants of the female parent selection in the following characteristics:

1. Plants of the new *Aster* are faster growing than plants of the female parent selection.
2. Plants of the new *Aster* flower earlier and more freely than plants of the female parent selection.
3. Plants of the new *Aster* have larger inflorescences than plants of the female parent selection.
4. Plants of the new *Aster* are more resistant to Powdery Mildew than plants of the female parent selection.

Plants of the new *Aster* can be compared to plants of *Aster hybrida* 'Esmore', disclosed in U.S. Plant Pat. No. 16,195. In side-by-side comparisons conducted in El Quinche, Pichincha, Ecuador, plants of the new *Aster* differed from plants of 'Esmore' in the following characteristics:

1. Plants of the new *Aster* were more freely branching than plants of 'Esmore'.
2. Plants of the new *Aster* had ovate-shaped leaves whereas plants of 'Esmore' had lanceolate-shaped leaves.
3. Plants of the new *Aster* flowered earlier than plants of 'Esmore'.
4. Plants of the new *Aster* were more freely flowering than plants of 'Esmore'.

BRIEF DESCRIPTION OF THE PHOTOGRAPHS

The accompanying colored photographs illustrate the overall appearance of the new *Aster* plant. These photographs show the colors as true as it is reasonably possible to obtain in colored reproductions of this type. Colors in the photographs may differ slightly from the color values cited in the detailed botanical description which accurately describe the colors of the new *Aster* plant.

The photograph at the center left of the sheet comprises a side perspective view of a typical flowering stem of 'ESM A002'.

The photograph at the upper right of the sheet is a close-up view of the upper surface of a typical inflorescence of 'ESM A002'.

The photographs at the lower right of the sheet are close-up views of typical developed and opening inflorescences of 'ESM A002' and 'Esmore'.

The photograph at the lower left of the sheet is a close-up view of the upper and lower surfaces of typical leaves of 'ESM A002'.

DETAILED BOTANICAL DESCRIPTION

The aforementioned photographs and following observations and measurements describe plants grown during the spring in El Quinche, Pichincha, Ecuador, under commercial practice in an outdoor nursery. During the production of the plants, day temperatures ranged from 12° C. to 30° C. and night temperatures ranged from 5° C. to 12° C. Plants were twelve weeks old when the photographs and the description were taken. In the following description, color references are made to The Royal Horticultural Society Colour Chart, 2001 Edition, except where general terms of ordinary dictionary significance are used.

Botanical classification: *Aster hybrida* 'ESM A002'.

Parentage:

*Female, or seed, parent.*—Proprietary selection of *Aster hybrida* identified as Line 51, not patented.

*Male, or pollen, parent.*—Unknown selection of *Aster hybrida*, not patented.

Propagation:

*Type.*—Terminal vegetative cuttings.

*Time to initiate roots.*—About 12 to 16 days at 17° C. to 25° C.

*Time to produce a rooted young plant.*—About 21 to 55 days at 17° C. to 25° C.

*Root description.*—Fine, fibrous; color close to N199D when dried.

*Rooting habit.*—Freely branching, moderately dense.

Plant description:

*Appearance.*—Herbaceous single-type cut flower *Aster*; flowering stems upright and strong; vigorous growth habit; symmetrical and uniform branching habit with long lateral branches; uniform and freely flowering habit.

*Plant height.*—About 90 cm.

*Plant width.*—About 28 cm.

*Lateral branches.*—Quantity per plant: About eleven. Length: About 62 cm. Diameter: About 4.3 mm. Internode length: About 3 cm. Strength: Strong. Texture: Pubescent. Color: Close to 144A.

Foliage description:

*Arrangement.*—Alternate, simple; sessile.

*Length.*—About 13 cm.

*Width.*—About 1.2 cm.

*Shape.*—Ovate.

*Apex.*—Acute.

*Base.*—Attenuate.

*Margin.*—Finely serrate.

*Texture, upper and lower surfaces.*—Glabrous, smooth.

*Color.*—Developing leaves, upper surface: Close to 147A to 137A. Developing leaves, lower surface: Close to 137A. Fully expanded leaves, upper surface: Close to 137A; venation, close to 145D. Fully expanded leaves, lower surface: Close to 137B; venation, close to 146B.

Inflorescence description:

*Appearance/habit.*—Single-type inflorescence form with elliptic-shaped ray florets; inflorescences terminal or axillary; disc and ray florets develop acropetally on a capitulum; inflorescences face mostly upright; uniform and freely flowering habit, about 200 inflorescences develop per lateral branch.

*Fragrance.*—Not detected.

*Flowering response.*—Plants flower year-round in Ecuador; plants begin flowering about ten weeks after planting.

*Postproduction longevity.*—Inflorescences maintain good color and substance for about nine to ten days as a cut flower and about 40 days on the plant; inflorescences persistent.

*Inflorescence bud.*—Height: About 6 mm. Diameter: About 5 mm. Shape: Nearly globose. Color: Close to 137B to 144A; towards the apex, close to N79A. Inflorescence size: Diameter: About 2.4 cm. Depth (height): About 1 cm. Diameter of disc: About 1 cm. Receptacle height: About 6 mm. Receptacle diameter: About 6 mm. Ray florets: Number of ray florets per inflorescence/arrangement: About 26 arranged in two whorls. Length: About 1.1 cm. Width: About 3 mm. Shape: Elliptic. Apex: Acute to obtuse with some emargination. Base: Attenuate. Margin: Entire. Texture, upper and lower surfaces: Smooth, glabrous. Orientation: Initially upright, then mostly horizontal. Aspect: Straight to incurved. Color: When opening, upper and lower surfaces: Close to 155B; towards the base, close to 145C. Fully opened, upper and lower surfaces: Close to 155C; towards the base, close to 157B. Disc florets: Number of disc florets per inflorescence/arrangement: About 30 massed at center of receptacle. Length: About 9 mm. Diameter, apex: About 2.5 mm. Diameter, base: About 0.7 mm. Shape: Tubular, salverform, elongated. Apex: Five lobes; lobes acute. Color, when opening: Apex: Close to N144A. Mid-section and base: Close to 153B to 151A. Color, mature: Apex: Close to 153C. Mid-section and base: Close to 145D.

*Phyllaries.*—Number of phyllaries per inflorescence/arrangement: About 40 arranged in two to three whorls. Length: About 5 mm. Width: About 1 mm. Shape: Narrowly deltoid. Apex: Acute. Base: Truncate. Texture, upper surface: Pubescent. Texture, lower surface: Smooth, glabrous. Color, upper and lower surfaces: Close to 137A to 145C.

*Peduncles.*—Length, terminal peduncle: About 1 cm. Length, fourth peduncle: About 5 mm. Length, seventh peduncle: About 8 mm. Diameter: About 4.3 mm. Aspect: Erect to about 37° from vertical. Strength: Moderately strong. Texture: Pubescent. Color: Close to 146A to 137A.

*Reproductive organs.*—Androecium: Present on disc florets only. Quantity per disc floret: Four. Filament length: About 1.4 mm. Filament color: Close to 157D to 155C. Anther shape: Lanceolate. Anther length: About 1.3 mm. Anther color: Close to 151C. Pollen amount: Scarce. Pollen color: Close to 151C. Gynoecium: Present on both ray and disc florets. Quantity per floret: One. Pistil length: About 9 mm. Stigma shape: Bilobed; lobes linear. Stigma color: Close to 151D. Style length: About 5.2 mm. Style color: Close to 157A. Ovary color: Close to 150D.

*Seeds/fruits*.—Seed and fruit development have not been observed on plants of the new *Aster*.

Disease/pest resistance: Plants of the new *Aster* have been observed to be somewhat resistant to Alternaria and Botrytis. Plants of the new *Aster* have not been observed to be resistant to pests and other pathogens common to *Asters*.

Temperature tolerance: Plants of the new *Aster* have been observed to tolerate temperatures from about 5° C. to about 30° C.

It is claimed:

1. A new and distinct *Aster* plant named 'ESM A002' as illustrated and described.

* * * * *

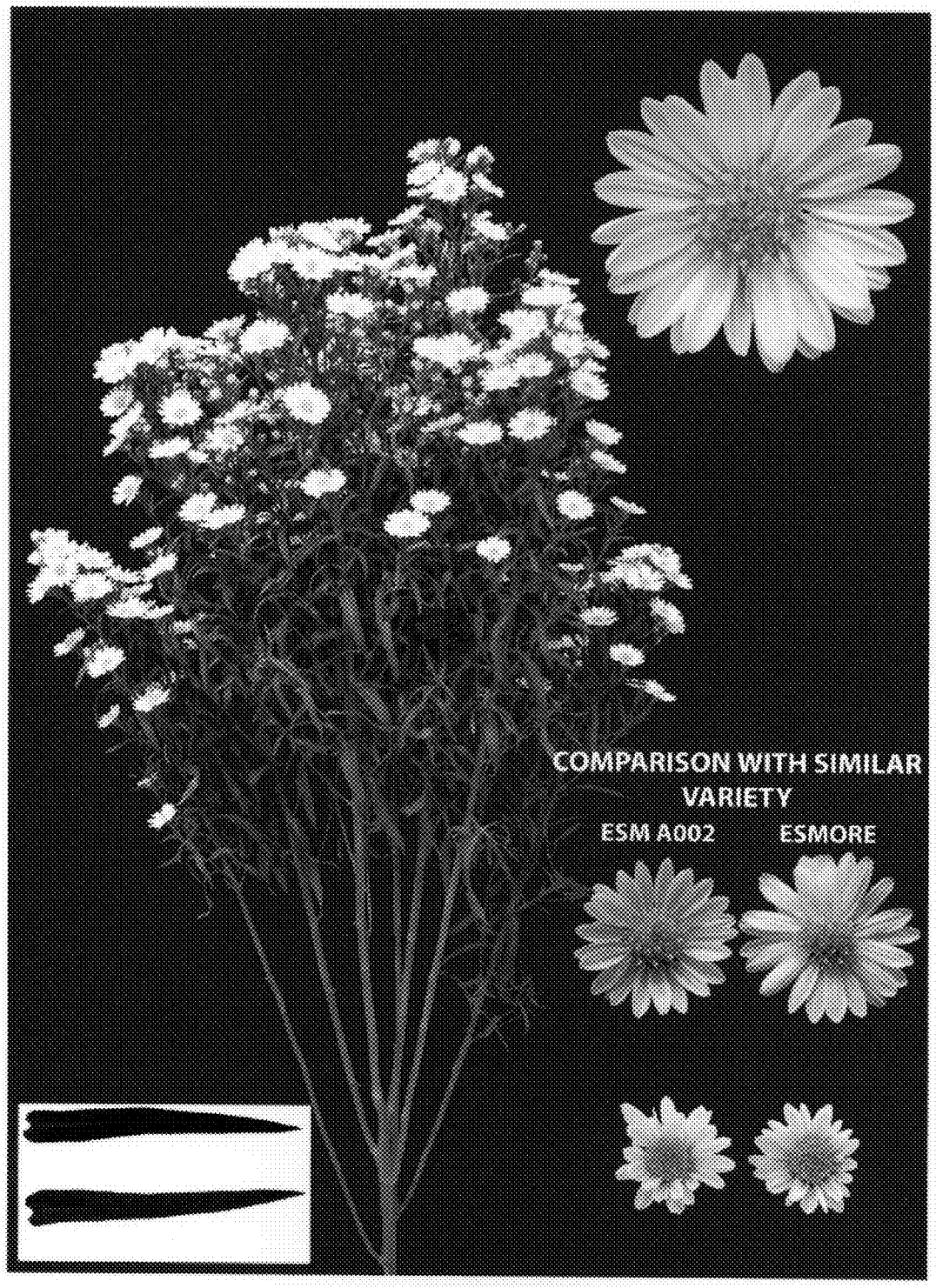
COMPARISON WITH SIMILAR
VARIETY
ESM A002
ESMORE